(12) United States Patent
Sasso (10) Patent No.: US 10,428,399 B2
(45) Date of Patent: Oct. 1, 2019

(54) IMMERSION PROBE AND ASSEMBLY OF IMMERSION SUBLANCE AND IMMERSION PROBE FOR A CONVERTER FURNACE

(71) Applicant: ECIL MET TEC LTDA., Piedade (BR)

(72) Inventor: Peterney Sasso, Piedade (BR)

(73) Assignee: ECIL MET TEC LTDA., Piedade (BR)

(*) Notice: Subject to any disclaimer, the term of this patent is extended or adjusted under 35 U.S.C. 154(b) by 187 days.

(21) Appl. No.: 15/539,853

(22) PCT Filed: Dec. 24, 2015

(86) PCT No.: PCT/EP2015/081232
§ 371 (c)(1),
(2) Date: Jun. 26, 2017

(87) PCT Pub. No.: WO2016/107821
PCT Pub. Date: Jul. 7, 2016

(65) Prior Publication Data
US 2018/0002770 A1   Jan. 4, 2018

(30) Foreign Application Priority Data
Dec. 30, 2014 (BR) .............. 102014033086

(51) Int. Cl.
*C21C 5/46* (2006.01)
*G01N 1/14* (2006.01)
(Continued)

(52) U.S. Cl.
CPC ............ *C21C 5/4673* (2013.01); *F27D 19/00* (2013.01); *G01K 13/12* (2013.01); *G01N 1/125* (2013.01);
(Continued)

(58) Field of Classification Search
CPC ....... C12C 5/4673; F27D 19/00; G01K 13/12; G01N 1/125; G01N 1/1409; G01N 33/205
USPC ......... 266/75, 83, 87, 89, 99, 225; 73/17.07, 73/700, 866.5, 863.31, 864.31, 864.53; 374/159
See application file for complete search history.

(56) References Cited

U.S. PATENT DOCUMENTS 4,566,343 A * 1/1986 Theuwis ............... C21C 5/4673
                                                    73/864.59
5,789,910 A   8/1998 Guthrie
(Continued)

FOREIGN PATENT DOCUMENTS

EP          0069433 A1   1/1983

*Primary Examiner* — Scott R Kastler
*Assistant Examiner* — Michael Aboagye
(74) *Attorney, Agent, or Firm* — Thomas Clinton; Donald M. Satina (57) ABSTRACT

An immersion probe with a variable connection length is configured to compensate for longitudinal and/or radial length variations in an immersion sublance connected to the immersion probe. The immersion probe is characterized by an adjustable portion that changes length upon engagement with a coupling end of an immersion sublance. The immersion probe can have a sensor head. An immersion assembly of the immersion probe connected to an immersion sublance can be used to take measurements or samples of molten metal in a converter furnace.

19 Claims, 9 Drawing Sheets

(51) Int. Cl.
    *G01K 13/12*      (2006.01)
    *G01N 33/20*      (2019.01)
    *G01N 1/12*      (2006.01)
    *C21C 5/54*      (2006.01)
    *F27D 21/00*      (2006.01)
    *C21C 5/52*      (2006.01)
    *G01N 33/205*      (2019.01)
    *F27D 19/00*      (2006.01)

(52) U.S. Cl.
    CPC ......... *G01N 1/1409* (2013.01); *G01N 33/205* (2019.01); *C21C 5/54* (2013.01); *C21C 2005/5288* (2013.01); *F27D 21/0014* (2013.01); *F27D 2019/0003* (2013.01); *F27D 2019/0006* (2013.01); *F27D 2019/0028* (2013.01); *Y02P 10/216* (2015.11)

(56) References Cited

U.S. PATENT DOCUMENTS

| | | | |
|---|---|---|---|
| 7,272,983 B2 * | 9/2007 | Caderas | ................ F15B 15/261 73/866.5 |
| 7,370,544 B2 | 5/2008 | Neyens et al. | |
| 8,479,579 B2 * | 7/2013 | Neyens | ................ G01N 33/205 73/700 |
| 2007/0173117 A1 | 7/2007 | Dams et al. | |
| 2013/0322489 A1 * | 12/2013 | Cuypers | ................ B22D 2/006 374/159 |

\* cited by examiner

IMMERSION PROBE AND ASSEMBLY OF IMMERSION SUBLANCE AND IMMERSION PROBE FOR A CONVERTER FURNACE

CROSS-REFERENCE TO RELATED APPLICATIONS

This application is a U.S. national stage application, filed under 35 U.S.C. § 371, of International Application No. PCT/EP2015/081232, which was filed on Dec. 24, 2015, and which claims priority to Brazil Patent Application No. BR 10 2014 033086 0, which was filed on Dec. 30, 2014, the contents of each of which are incorporated by reference into this specification.

FIELD OF THE INVENTION

The present invention relates to an immersion probe and an assembly of an immersion sublance and an immersion probe to perform measurements and/or take samples out of a converter furnace filled with molten metal. The immersion probe is configured to feature a variable length.

BACKGROUND OF THE INVENTION

Immersion sublances and immersion probes are broadly used in converter furnaces during steelmaking processes. Typically, pig iron and scrap metal are discharged into the converter furnace, which fuses them together at a high temperature (e.g., 1600 to 1750° C.), thus producing steel.

In order to produce a high quality product having ideal chemical characteristics, the molten metal has to be subjected to several chemical analyses. The aim is to monitor all the chemical elements contained in the steel, for example, by controlling, among others, the carbon, carbon equivalents and silicon concentration, or by monitoring the hardness, resistance, machinabily, temperature, and/or oxidation level.

Such chemical analyses are performed by means of sensing or sampling the molten metal, those operations being performed by sensors located at the end of an immersion probe.

Conventionally, during the production of molten metal, a blowing lance is used to blow oxygen inside the converter furnace at supersonic speed onto molten slag and molten metal.

In parallel, the assembly of an immersion sublance and an immersion probe is inserted from the external environment into the inside of the converter furnace following a longitudinal direction, such that only the immersion probe of said assembly is submerged into molten slag and subsequently into molten metal. Once in contact with molten metal, the immersion probe is able to perform measurements and/or take samples of molten metal by means of sensors or sampling chambers. Upon fulfillment of those tasks, the assembly of the immersion sublance and the immersion probe is taken out of the converter furnace, and the immersion probe is then disconnected from the immersion sublance and then discarded.

The connection of the immersion probe to the immersion sublance is performed before the insertion of the assembly into the converter furnace, said connection being partially automated.

As previously mentioned, the immersion probe is used only once during the immersion and/or measurement process. On the other hand, the immersion sublance can be reused, for it is provided with a longer service life.

Considering that the immersion sublance is used for several immersions and/or measurements, deformations due to harsh ambient conditions and high temperatures inside the converter furnace have been observed after several immersions and/or measurements by the sublance. Such deficiencies are quite common and severe, resulting in difficulty connecting a new immersion probe to the immersion sublance.

More specifically, a deformed immersion sublance can present connection problems with a new immersion probe, resulting in clearance problems between the sublance holder and the immersion probe. Such characteristics are not desirable, and can lead to various problems.

Since the immersion probe structure is typically made of cardboard and does not possess precise dimensions, it has been observed that the immersion probe cannot completely cover the immersion sublance holder. Furthermore, depending on the climatic conditions, as well as the storage location of the immersion probes, it is known that deformations can occur on the cardboard constituting the probes' casings, creating radial or longitudinal variations. Considering this problem, it is known that when the assembly of an immersion sublance and an immersion probe is inserted into the converter furnace, some molten metal splashes might land on the sublance holder, making the connection to a new immersion probe difficult.

In order to avoid this problem, an attempt has been made in the art to counter the deformation of the immersion sublance. The European Patent EP-A1-69433 describes a sublance presenting a fixed upper end and a lower end which can rotate. It specifically discloses that the lower portion of the immersion sublance gets deformed after the first immersion in molten metal, then the sublance is taken out of the converter furnace and its lower end is rotated 180°. After said rotation, the sublance is then immersed anew. According to the teachings of European Patent EP-A1-69433, this feature allows the lower portion to come back to its original position (before the first immersion).

Another known solution is described by the U.S. Pat. No. 4,566,343. This patent discloses an immersion sensor comprising a rubber seal designed to prevent molten metal from penetrating into the immersion sublance.

In addition, another solution aimed at improving the connection between the immersion probe and the sublance holder is also known in the art. US-B2-7370544 describes the use of a spring or an elastic ring on the sublance holder. This solution is problematic, considering that the immersion sublances currently commercialized require some adjustments in order to accommodate the spring or the elastic ring. In this way, it becomes mandatory to stop the measurement process in order to adapt the sublance described in US-B2-7370544.

Considering the above solutions, it is observed that in the state of the art, the use of an immersion probe with a variable connection length, able to compensate for length variations in the longitudinal and/or radial directions of the immersion sublances, is not known.

Furthermore, the current state of the art provides no solution for the use of an immersion probe with a variable connection length without requiring the adaptation of the immersion sublances, such that immersion sublances currently commercialized could be used without requiring any adaptation.

BRIEF SUMMARY OF THE INVENTION

The first aim of the present invention is to provide an immersion probe enabling a greater connection efficiency with an immersion sublance holder.

The second aim of the present invention is to provide an immersion probe that can be connected to immersion sublances currently commercialized without any need to adapt them.

Another aim of the present invention is to provide an immersion probe that can be connected to immersion sublances with a variable connection length.

Yet another aim of the present invention is to provide an immersion probe that can be connected to immersion sublances that have been deformed by consecutive immersions into a converter furnace.

In addition, the present invention also aims at providing an immersion probe that can prevent molten metal from sticking onto an immersion sublance holder.

Providing an immersion probe that prevents connection defects or clearance problems with an immersion sublance is also among the aims of this invention.

Finally, the present invention aims at compensating for the longitudinal and/or radial length variations of an immersion sublance upon connection.

The aims of the present invention are achieved by an immersion assembly for a converter furnace comprising an immersion sublance and an immersion probe. The immersion sublance comprises a guide connecting end, the guide connecting end configured to couple to a first coupling end of a sublance holder. The sublance holder extends longitudinally from the first coupling end to a second coupling end, wherein the sublance holder connects to the immersion probe through a connection between the second coupling end of the sublance holder and an adjustable portion of the immersion probe.

The aims of the present invention are also achieved by an immersion probe for a converter furnace comprising a casing and an adjustable portion. The casing features an internal cavity in order to receive the adjustable portion, wherein the adjustable portion extends longitudinally along the internal cavity of the casing, from a connecting portion to a fixed portion. The connecting portion and the fixed portion are attached to one another through an elastic portion, wherein the elastic portion is configured to change the length of the adjustable portion once a first contact point has been established with the surface of the connecting portion.

BRIEF DESCRIPTION OF THE DRAWINGS

Various features and characteristics of the invention described in this specification may be more thoroughly understood by reference to the accompanying figures, in which.

DETAILED DESCRIPTION OF THE INVENTION

Figure 1:
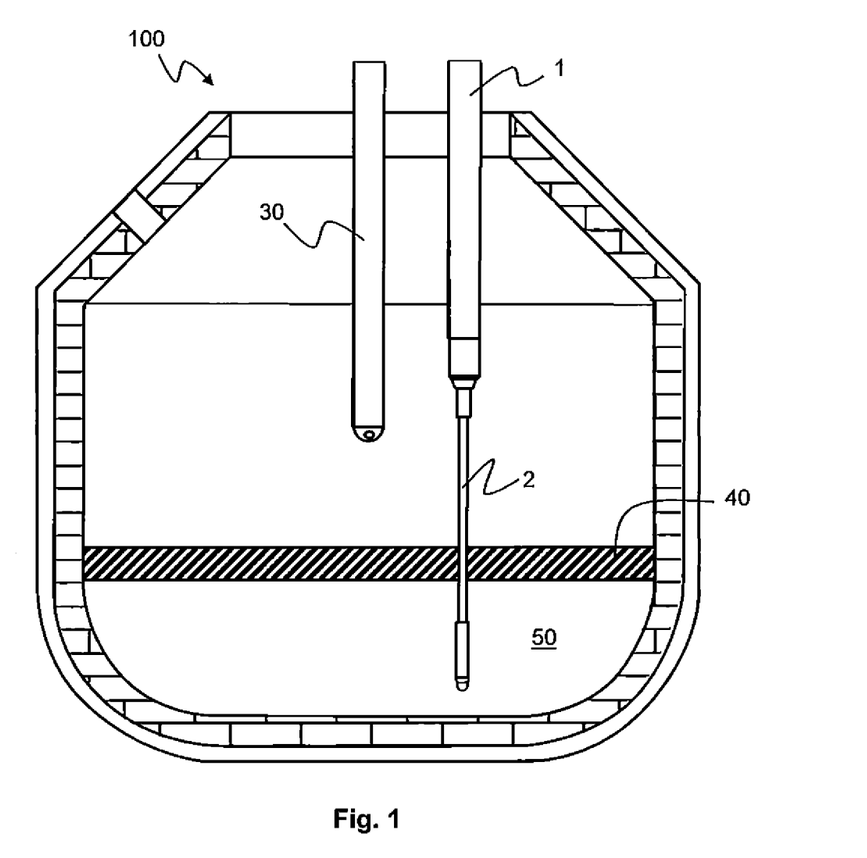
FIG. 1 is an inside view of a converter furnace with a blowing lance and an assembly comprising an immersion sublance and an immersion probe immersed in molten metal.

FIG. 1 illustrates an inside view of a converter furnace 100 used in the steel industry for producing and refining steel. During the production of molten metal, a blowing lance 30 is used inside the converter furnace 100, said blowing lance 30 being used for injecting oxygen at supersonic speed on molten slag 40 and molten metal 50.

Still referring to FIG. 1, an assembly formed by an immersion sublance 1 connected to an immersion probe 2 is shown. The assembly formed by said components is inserted into the inside of a converter furnace 100. The assembly of the immersion sublance 1 and the immersion probe 2 is configured to extend longitudinally from the external environment into the direction of the inside of the converter furnace 100. More specifically, the assembly extends such that the immersion probe 2 is immersed into the molten metal 50 lying underneath the molten slag 40. When immersed, the immersion probe 2 performs measurements and/or takes samples of molten metal 50. Afterwards, the immersion probe 2 is removed from the converter furnace 100, disconnected from the sublance 1, and then discarded.

Figure 2:
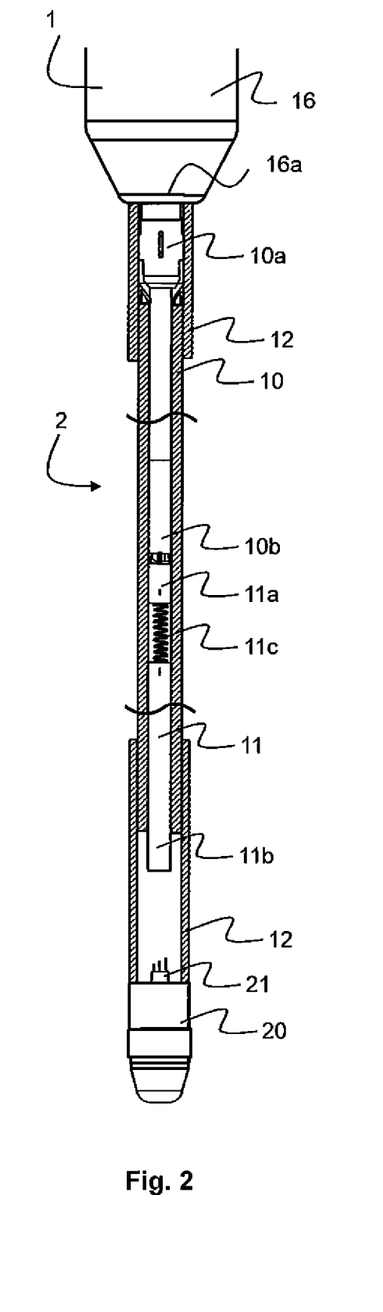
FIG. 2 is a representation of one configuration of an assembly comprising an immersion sublance and an immersion probe according to the present invention.

Referring to FIG. 2, an assembly comprising an immersion sublance 1 and an immersion probe 2 is shown in one configuration of the present invention, wherein the connection between both elements constituting the assembly is shown in detail.

When the immersion sublance 1 is used for measurement of molten metal 50 (see FIG. 1), the measurement is performed using sensors 21 located at the end of the immersion probe 2 to be immersed in the molten metal 50 (see FIG. 2). Generally, the sensors 21 are connected to a measuring instrument (not shown), located in the surrounding environment of the converter furnace 100. The connection between the sensors 21 and the measuring instrument (not shown) being realized by contact lines that run through the inside of the immersion probe 2 and the immersion sublance 1 up to the external environment. After the measurement, the immersion probe 2 is removed from the converter furnace 100, disconnected from the sublance 1, and then discarded.

Figure 4:
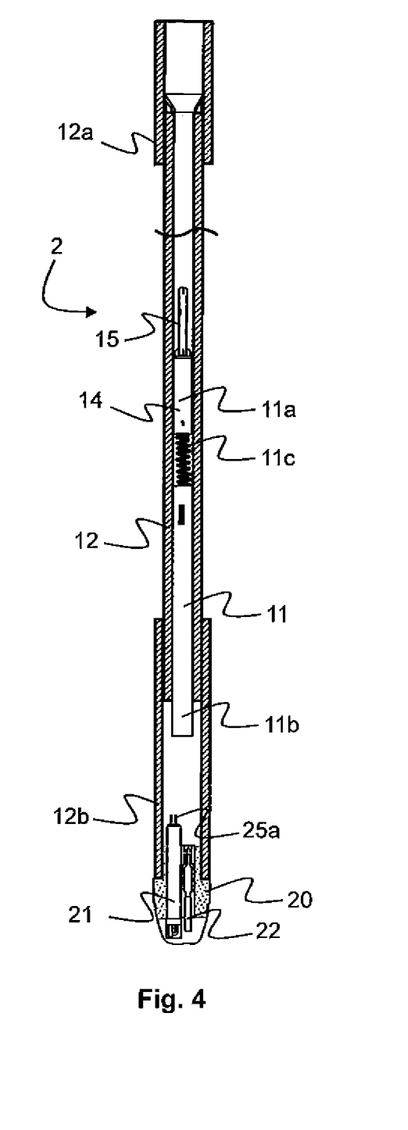
FIG. 4 is a representation of one configuration of an immersion probe when disconnected from an immersion sublance.

In implementation, where the immersion sublance 1 is used to take samples of the molten metal 50 (see FIG. 1), the samples are collected in a chamber 22 located at the end of the immersion probe 2 to be immersed in the molten metal 50 (see FIG. 4). After the sampling, the molten metal 50 that has been collected is removed from the converter furnace 100 for further analysis, the immersion probe 2 is disconnected from the sublance 1, and then discarded.

Alternatively, the immersion sublance 1 can simultaneously perform measuring and sampling of the molten metal 50 using the chamber 22 and the sensors 21 as previously described.

In order to provide a better understanding of the present invention, the immersion sublance 1 and the immersion probe 2 are first described separately, and then the connection of both elements to form an immersion assembly comprising the immersion sublance 1 and the immersion probe 2 will be described.

Figure 3A:
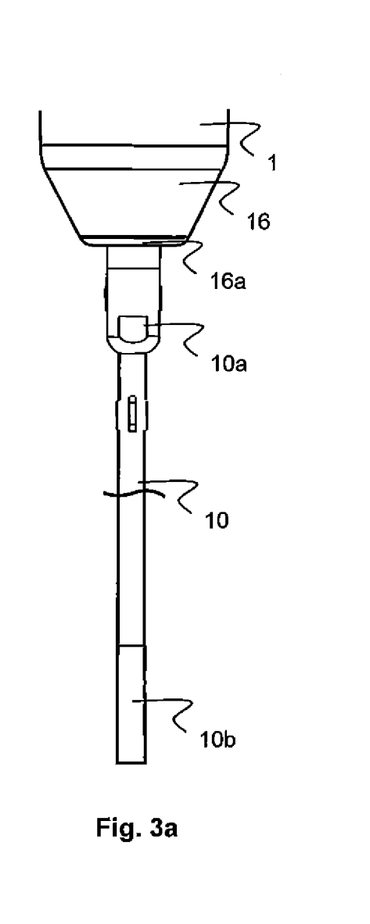
FIG. 3a is a representation of one configuration of an immersion sublance when disconnected from an immersion probe.
Figure 3B:
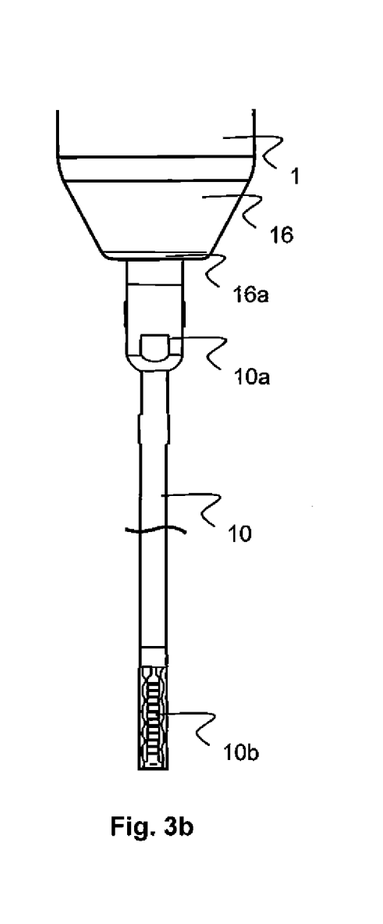
FIG. 3b is a representation of the immersion sublance when disconnected from the immersion probe, as shown in FIG. 3a, illustrating one configuration of the internal cavity of the sublance holder.

One configuration of an immersion sublance 1 is shown in FIGS. 3a and 3b.

FIGS. 3a and 3b show the mechanical structure of the immersion sublance 1, the sublance 1 comprising a guide 16 and a sublance holder 10.

In one configuration of the present invention, the guide 16 has a substantially cylindrical/tubular shape, being hollow along its whole length. Such a configuration creates an internal cavity for the passage of contact lines connected to sensors 21 (see FIG. 2) up to the surrounding environment and subsequently to a measuring instrument (not shown).

The aforementioned guide 16 may be made from metallic materials able to withstand the typical high temperatures (e.g., 1600 to 1750° C.) of a converter furnace 100.

Still referring to FIGS. 3a and 3b, in one configuration, the guide 16 has a guide connecting end 16a on its portion that is closest to the molten metal in the converter furnace 100 during use. As shown, the guide connecting end 16a is coupled to the sublance holder 10 of the sublance 1.

The sublance holder 10 can have a substantially cylindrical/tubular shape, and the sublance holder 10 can extend longitudinally from a first coupling end 10a, in a direction of the bottom of the converter furnace 100, down to a second coupling end 10b.

It can be observed that the first coupling end 10a is coupled to the guide connecting end 16a, such that the diameter of the guide connecting and 16a is equal to the external diameter of the first coupling end 10a, thus presenting a perfect coupling.

Regarding the second coupling end 10b, as described below, it presents an external diameter similar to the external diameter of the internal cavity of the immersion probe 2.

Figure 7A:
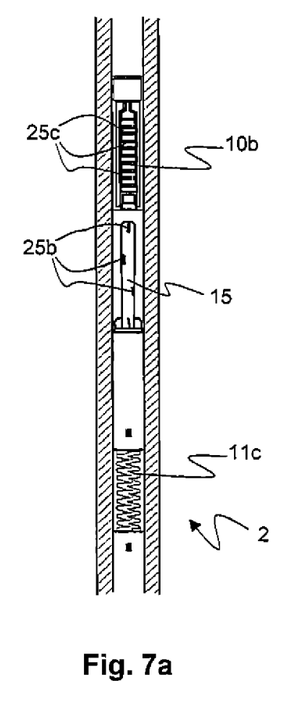
FIGS. 7a, 7b, 7c, and 7d are step-by-step representations showing the establishment of a first contact point between a sublance holder and an immersion probe in one configuration of the present invention.
Figure 7B:
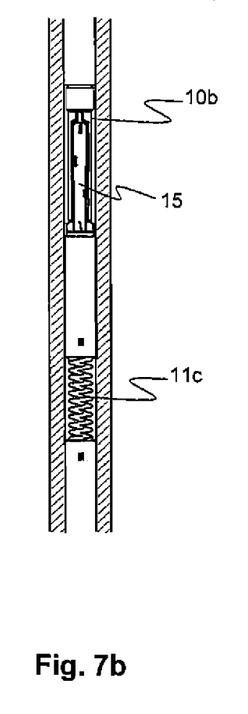
Figure 7C:
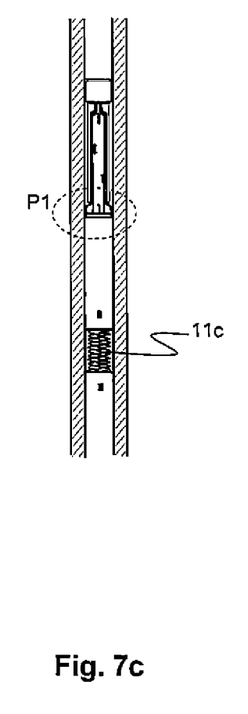
Figure 7D:
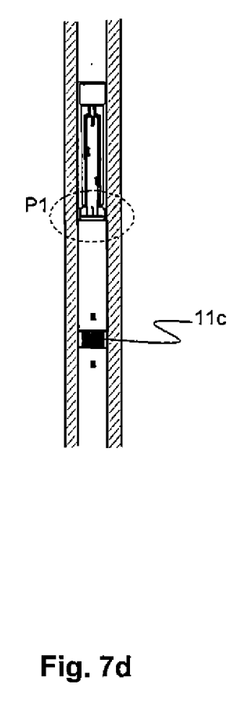

Referring to FIG. 3b, in one configuration, an internal cavity of the immersion sublance 1 is located at the second coupling end 10b. Furthermore, the internal cavity can feature at least one holder contact line 25c (see FIG. 7a), at least one of the holder contact lines 25c being arranged circumferentially around the inner wall of the internal cavity of the sublance holder 10 at the second coupling end 10b. At least one holder contact line 25c is connected to the measuring instrument located in the surrounding environment of the converter furnace 100.

The immersion sublance 1 having been described above, the immersion probe 2 will now be described below. In one configuration, the immersion probe 2 is illustrated in FIG. 4.

FIG. 4 shows the mechanical structure of the immersion probe 2, the immersion probe comprising a casing 12, an adjustable portion 11, and a sensing head 20.

The casing 12 of the immersion sublance 2 can be made from cardboard and can feature different lengths or diameters, these being dimensioned according to the user.

The casing 12 is designed with several layers of cardboard, such that the casing 12 of the immersion probe 2 does not completely disintegrate when the immersion probe 2 is immersed into molten metal 50 (see FIG. 1). Considering that the immersion lasts a few seconds, the structure of the casing 12 formed of several layers of cardboard is able to withstand the typical high temperatures (e.g., 1600 to 1700° C.) of a converter furnace 100.

In one configuration, the casing 12 features a substantially cylindrical/tubular shape along its whole length, such a configuration allowing the creation of an internal cavity to receive the adjustable portion 11, the internal diameter being wide enough to receive the above referred to adjustable portion 11.

Furthermore, it can also be observed from FIG. 4 that, in one configuration, the casing 12 comprises a casing upper portion 12a and a casing lower portion 12b. Considering that both portions 12a and 12b feature the same diameter, it is observed that an intermediate portion of the casing 12 features a smaller diameter.

Figure 10:
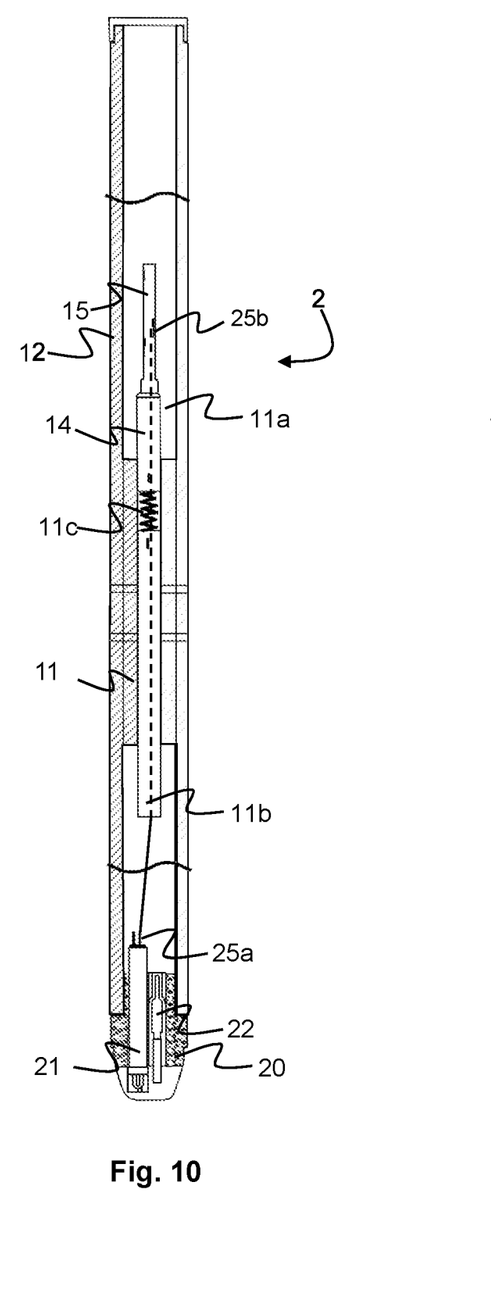
FIG. 10 is a representation of a second embodiment of the present invention.
Figure 11:
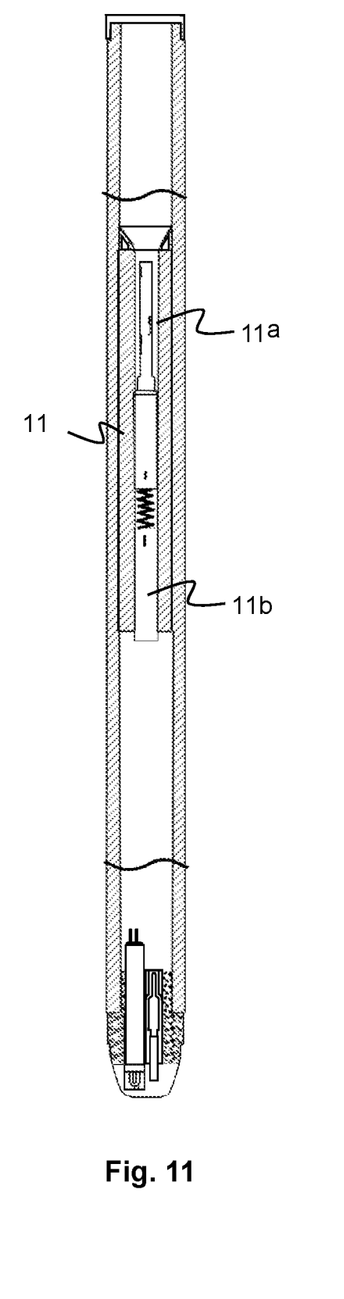
FIG. 11 is a representation of a third embodiment of the present invention.

Alternatively, as shown in FIGS. 10 and 11, the casing 12 can feature a constant diameter along its whole length.

Still referring to FIG. 4, the adjustable portion 11 extends longitudinally along the inside of the internal cavity of the casing 12 from a connecting portion 11a to a fixed portion 11b. The connecting portion 11a is located close to the casing upper portion 12a, and the fixed portion 11b is located close to the casing lower portion 12b. The connecting portion 11a and the fixed portion 11b are associated to one another by means of an elastic portion 11c, such that the adjustable portion 11 features a variable length.

In one configuration, it is observed that the connecting portion 11a and the fixed portion 11b feature a substantially cylindrical/tubular shape comprising diameters smaller than or equal to the internal cavity of the casing 12.

The elastic portion 11c can comprise a spring, an elastic ring, an elastomer, or any other elastic material, able to compress and expand self by means of applying a force once a first contact point P1 is established, as shown in FIGS. 5a-5e, 6a-6e, and 7a-7d, and that will be subsequently described in detail below.

Still referring to FIG. 4, the connecting portion 11a comprises a connection base 14 and a connector 15. The connection base 14 is located at the end of the connecting portion 11a that is closest to the bottom of the converter furnace 100 when in use. The connector 15 is located at the end of the connecting portion 11a that is closest to the top of the converter furnace 100 when in use. The connection base 14 is attached to the connector 15 and the elastic portion 11c. The connector 15 extends from the connection base 14 of the connecting portion 11a the direction of the top of the converter furnace 100 when in use.

In one configuration, as shown in FIGS. 7a to 7d, the connector 15 is provided with at least one connector contact line 25b, the at least one connector contact line 25b being circumferentially located around the surface of the connector 15. As further described below, the at least one connector contact line 25b of the connector 15 will be connected to at least one holder contact line 25c of the sublance holder 10 when the immersion probe 2 is connected to the immersion sublance 1.

The dimensions of the connector 15 can be such that the connector 15 has a substantially smaller diameter than the connection base 14, and the connector 15 can have a diameter smaller than or equal to the diameter of the second coupling end 10b. The base 14 in turn presenting a diameter smaller or equal to the one of the second coupling end 10b of the sublance holder 10 of the immersion sublance 1. Such configuration provides a good connection between the immersion sublance 1 and the immersion probe 2, as further described below.

Referring again to FIG. 4, the fixed portion 11b extends from the elastic portion 11c towards the bottom of the converter furnace 100 when in use, and the fixed portion 11b is coupled to the casing lower portion 12b. The sensing head 20 is also coupled to the casing lower portion 12b.

Figure 9:
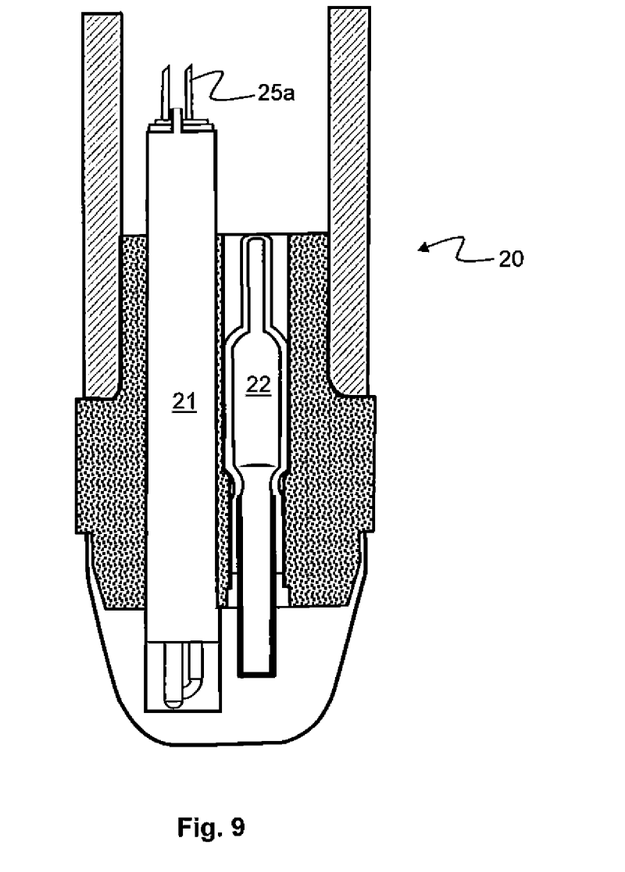
FIG. 9 is a representation of one configuration of a sensing head and its components comprising an immersion probe of the present invention.

In one configuration, as shown in FIG. 9, the sensing head 20 comprises at least one sensor 21, which could either be a temperature sensor, an oxygen sensor, or any other sensor useful-for molten metal chemical analyses. At least one sensor 21 is provided with at least one sensor contact line 25a, the sensor contact line 25a extending up through the fixed portion 11b and the elastic portion 11c to the connecting portion 11a, where the sensor contact line 25a is connected to at least one connector contact line 25b (see FIG. 10).a1

Additionally, the sensing head 20 can comprise a sampling chamber 22, the sampling chamber being configured to collect molten metal 50 when the immersion probe 2 is immersed, the collected molten metal 50 solidifying when the immersion probe 2 is taken out of the converter furnace 100.

The immersion sublance 1 and the immersion probe 2 having been described above, the connection between the immersion sublance 1 and the immersion probe 2 will now be described below, such connection resulting in an assembly comprising the immersion sublance 1 and the immersion probe 2.

During steelmaking processes in a converter furnace 100, the user must connect a new immersion probe 2 to the immersion sublance 1, this constituting an assembly of the immersion sublance 1 and the immersion probe 2.

Referring to FIGS. 5a to 5e and 6a to 6a, the connection of the immersion probe 2 to the immersion sublance 1 is show in a step-by-step manner, the main focus being only the guide connecting end 16a of the immersion sublance 1.

Figure 5A:
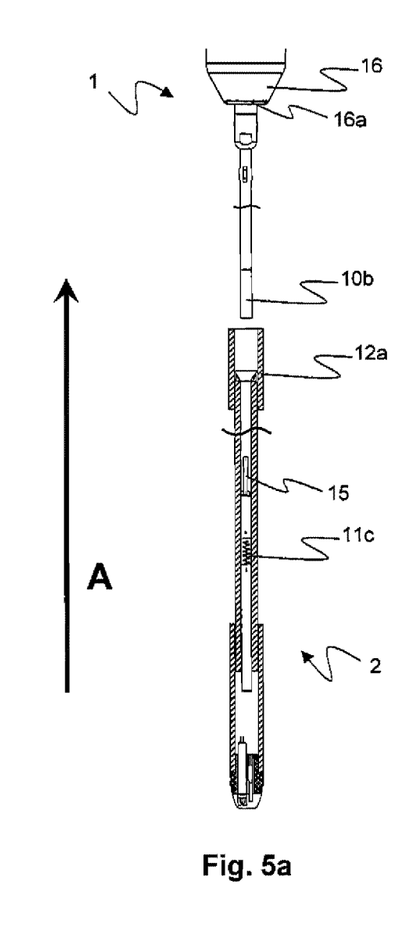
FIGS. 5a, 5b, 5c, 5d, and 5e are step-by-step representations showing how an immersion sublance is connected to an immersion probe in one configuration of the present invention.
Figure 6A:
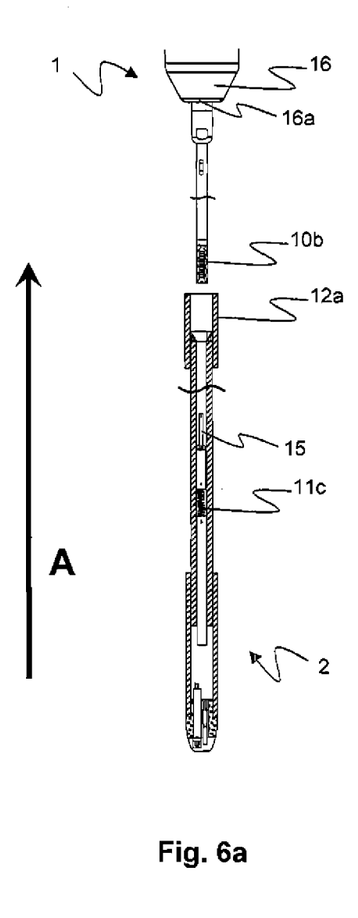
FIGS. 6a, 6b, 6c, 6d, and 6e are step-by-step representations showing how an immersion sublance is connected to an immersion probe in one configuration of the present invention, and illustrating in detail the internal cavity of a sublance holder.

FIGS. 5a and 6a illustrate a case where the immersion sublance 1 and the immersion probe 2 are completely disconnected. An arrow A represents the direction of motion of the immersion probe 2 and/or the immersion sublance 1 toward each other, typically performed by a user, to effect the connection of the elements.

Figure 5B:
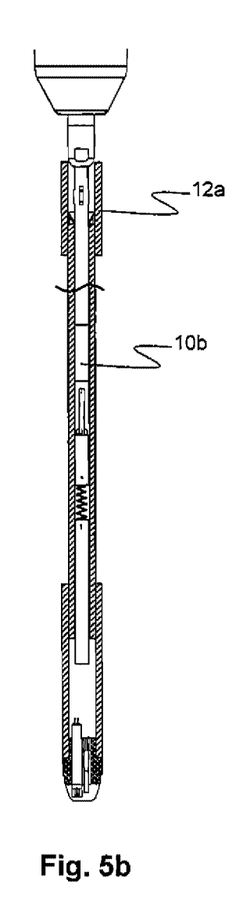
Figure 6B:
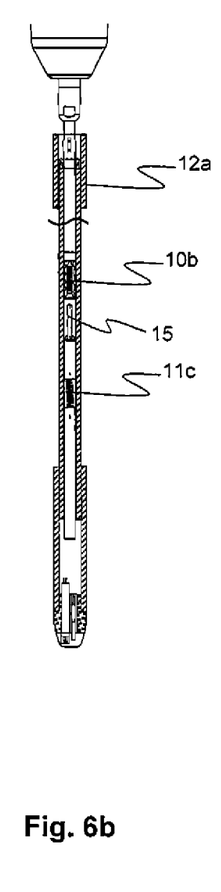

Once the immersion probe 2 has been moved in the direction of connection A, for example, the sublance holder 10 of the immersion sublance 1 is connected to the immersion probe 2. More specifically, the second coupling end 10b of the sublance holder 10 extends into the internal cavity of the immersion sublance 2 towards the adjustable portion 11, as shown in FIGS. 5b and 6b. As previously noted, the external diameter of the second coupling end 10b is smaller than or equal to the internal cavity of the immersion probe 2.

When the immersion probe 2 and the immersion sublance 1 are connected, the casing 12 of the immersion probe 2 will encase the sublance holder 10 of the immersion sublance 1 and the adjustable portion 11 of the immersion probe 2. Once the second coupling end 10b is inserted into the internal cavity of the immersion probe 2, the second coupling end 10b extends towards the connector 15 of the connecting portion 11a (see FIGS. 5b and 5c).

Figure 5C:
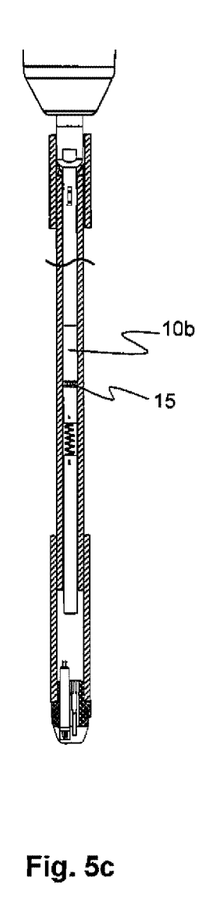
Figure 5D:
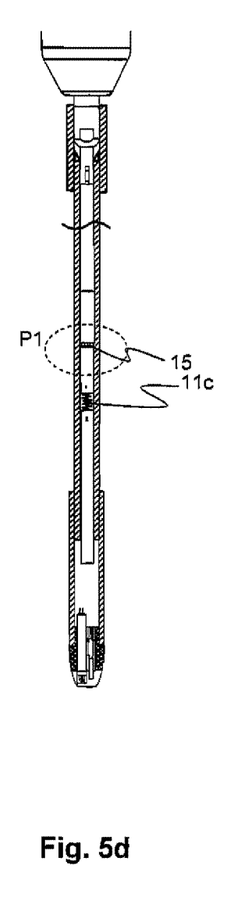
Figure 6C:
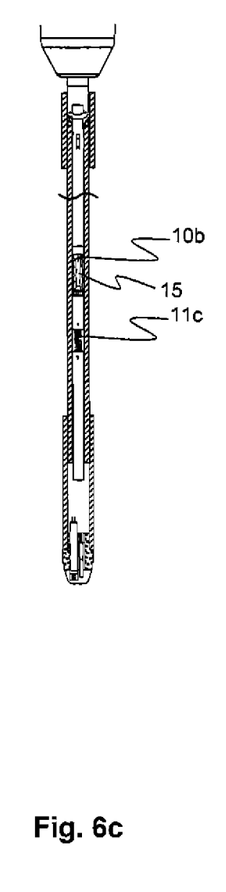
Figure 6D:
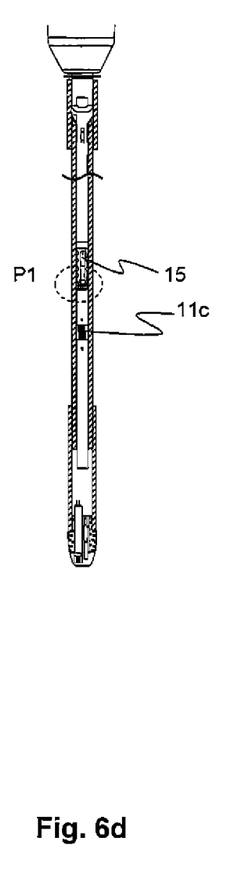

Considering that the connector 15 features a diameter equal to or smaller than the internal diameter of the second coupling end 10b, the connector 15 will extend towards and then into the internal cavity of the second coupling end 10b (see FIGS. 5c and 6c).

As shown in FIGS. 5b-5d and 6b-6d, the connector 15 will progressively extend into the internal cavity of the second coupling end 10b until the distal surface of the second coupling end 10b establishes a first contact point P1 with the proximal surface of the connection base 14 of the connecting portion 11a.

Such first contact point P1 is established by the connection base 14 of the connecting portion 11a, which has a diameter equal to the external diameter of the second coupling end 10b.

Still referring to FIGS. 5a-5e and 6a-6e, considering the movement of the immersion probe 2 in the direction of connection A, and the establishment of the first contact point P1, the elastic portion 11c will be compressed by further movement along direction A, and the length of the adjustable portion 11 will vary.

Furthermore, referring to from FIGS. 7a-7d, a detailed view of the connection between the connector 15 and the coupling end 10b is shown, as well as the connection of the connector contact lines 25b and the holder contact lines 25c. When the connector 15 is positioned in the internal cavity of the coupling end 10b, the connector contact lines 25b of the connector 15 connect themselves to the holder contact lines 25c located in the internal cavity of the coupling end 10b of the sublance holder 10. Such connection can be observed from FIGS. 7b and 7c. Still, it can be noted from FIGS. 7b and 7c that a connection between the respective contact lines 25b and 25c is realized when the first contact point P1 is established.

Figure 5E:
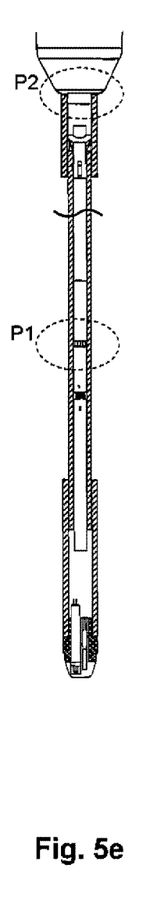
Figure 6E:
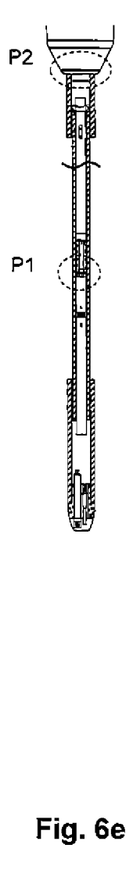
Figure 8A:
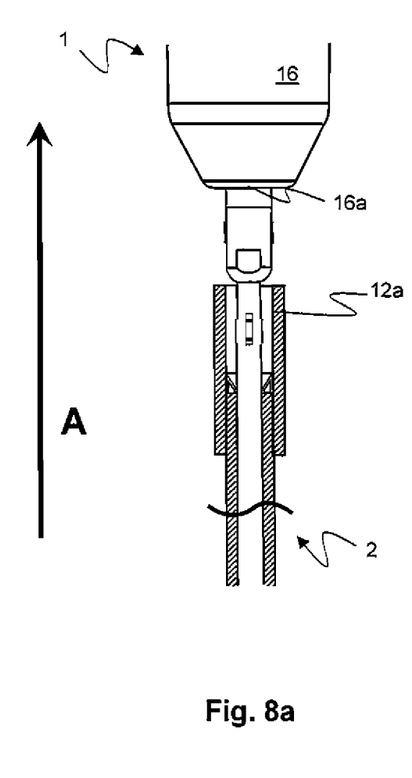
FIGS. 8a, 8b, 8c, and 8d are step-by-step representations showing the establishment of a second contact point between a sublance holder and an immersion probe in one configuration of the present invention.
Figure 8B:
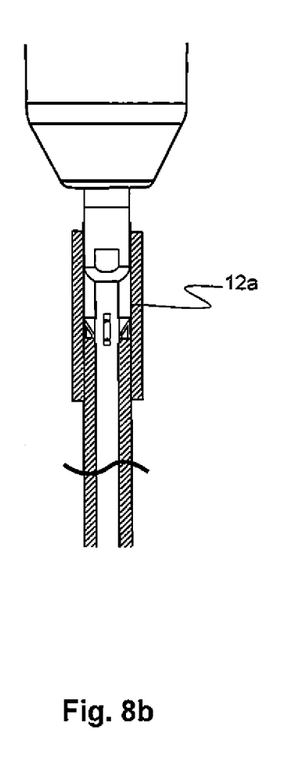
Figure 8C:
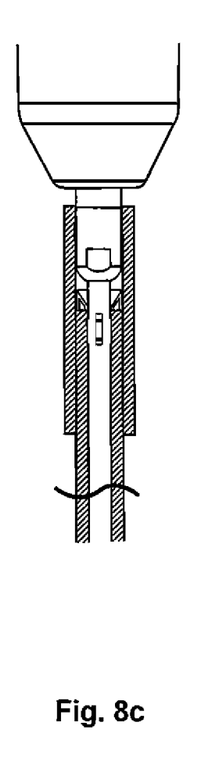
Figure 8D:
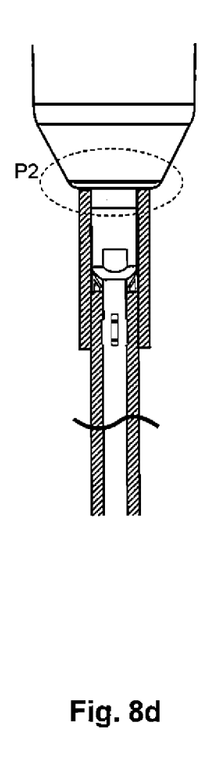

The elastic portion 11c is compressed until the casing upper portion 12a is connected to the guide connecting end 16a, as shown in FIGS. 5e, 6e, and 8d, where a second contact point P2 will be established.

A first contact point P1 and a second contact point P2 are established in the connection between the immersion sublance 1 and the immersion probe 2 such contact points P1, P2 establishing a connection to form the assembly of the immersion sublance 1 and the immersion probe 2. The assembly comprises an electrical connection between the respective contact lines 25b and 25c, and a mechanical connection between the casing upper portion 12a and the guide connecting end 16a.

After the connection of the immersion sublance 1 to the immersion probe 2, the assembly is ready to be used in the converter furnace 100 (see FIG. 1). Because of the use of the assembly in the inside of a converter furnace 100, the immersion sublance 1 can suffer deformations such as previously described.

As previously mentioned, the sublance holder 10, when exposed to high temperatures (e.g., 1600 to 1750° C.) and multiple, successive immersions, can suffer deformations, presenting radial or longitudinal variations.

Such longitudinal or radial variations are compensated for by the elastic portion 11c of the immersion probe 2 of the present invention. The exchange of the immersion sublance 1 thus not being required after being deformed, making it useable multiple limes with new immersion probes 1. The adjustable portion 11 features a length that varies with the length of the sublance holder 10 of the sublance 1.

The elastic portion 11c features a spring tension effect that is superior to the force required by the connector 15 on the second coupling end 10b. Furthermore, the elastic portion 11c features a spring tension effect that is inferior to the force required for the connection of the adjustable portion 11 of the immersion probe 2 to the sublance holder 10 of the sublance 1.

It is observed that even if the sublance holder 10 of the immersion sublance 1 was slightly deformed, the connection of the connector 15 to the second coupling end 10b could be accomplished because the elastic portion 11c allows the connector 15 to move along the longitudinal direction of the immersion probe 2.

Furthermore, the compensation of longitudinal or radial variations accomplished by the elastic portion 11c allows the user to use immersion sublances 1 that feature variations in connection length. In addition, considering that the casing 12 can be made out of cardboard and can have longitudinal or radial variations depending on the climatic conditions, as well as the storage location of the immersion probes, the elastic portion 11c will also compensate for such variations.

Various features and characteristics of the invention are described in this specification and illustrated in the drawings to provide an overall understanding of the invention. It is understood that the various features and characteristics described in this specification and illustrated in the drawings can be combined in any operable manner regardless of whether such features and characteristics are expressly described or illustrated in combination in this specification. The Inventor and the Applicant expressly intend such combinations of features and characteristics to be included within the scope of this specification, and further intend the claiming of such combinations of features and characteristics to not add new matter to the application. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims, and will comply with the written description requirement under 35 U.S.C. § 112(a). The invention described in this specification can comprise, consist of, or consist essentially of the various features and characteristics described in this specification.

The invention claimed is:

1. An immersion assembly for a converter furnace comprising: an immersion sublance comprising: a guide comprising a guide connecting end; and a sublance holder comprising a first coupling end and a second coupling end; wherein the guide connecting end of the guide is coupled to the first coupling end of the sublance holder; and wherein the sublance holder extends longitudinally from the first coupling end to the second coupling end; and an immersion probe comprising: a casing comprising an upper portion and having an internal cavity; and an adjustable portion located in the internal cavity, the adjustable portion comprising a connecting portion, an elastic portion, and a fixed portion, wherein the connecting portion is attached to the elastic portion and the elastic portion is attached to the fixed portion; and wherein the adjustable portion extends longitudinally along the internal cavity of the casing from the connecting portion to the fixed portion; wherein the second coupling end of the sublance holder of the immersion sublance is connected to the connecting portion of the adjustable portion of the immersion probe; wherein the connecting portion comprises a connector attached to a connection base, wherein the connector is located within the internal cavity of the casing, and wherein the connection base is attached to the elastic portion; wherein the elastic portion is disposed between the fixed portion and the connecting portion so that compression of the elastic portion decreases a length of the adjustable portion after a first contact point is established between a surface of the connection base of the connecting portion and a surface of the second coupling end of the sublance holder; and wherein the elastic portion is configured to compress until a second contact point is established between the upper portion of the casing of the immersion probe and the guide connecting end of the guide of the immersion sublance.

2. The immersion assembly of claim 1, wherein the adjustable portion has a variable length that varies with a length of the sublance holder.

3. The immersion assembly of claim 1, wherein the elastic portion comprises a spring, an elastic ring, an elastomer, or any other elastic material.

4. The immersion assembly of claim 3, wherein the elastic portion comprises a spring.

5. The immersion assembly of claim 1, wherein the immersion sublance and the immersion probe are substantially tubular in shape.

6. The immersion assembly of claim 5, wherein the immersion sublance and the immersion probe are substantially cylindrical in shape.

7. The immersion assembly of claim 1, wherein the second coupling end has an outside diameter and an internal cavity having an inside diameter; wherein the connection base has an outside diameter; and wherein the connector has an outside diameter; and wherein the outside diameter of the connection base is equal to the outside diameter of the second coupling end, and the outside diameter of the connector is less than the inside diameter of the internal cavity of the second coupling end.

8. The immersion assembly of claim 1, wherein the second coupling end has an internal cavity, and the connector extends along the internal cavity of the second coupling end until the first contact point is established between a surface of the connection base of the connecting portion and a surface of the second coupling end of the sublance holder.

9. The immersion assembly of claim 1, wherein the immersion probe further comprises a sensing head.

10. The immersion assembly of claim 9, wherein the sensing head comprises a temperature sensor, or an oxygen sensor, or a sampling chamber, or a combination of any thereof.

11. The immersion assembly of claim 9, wherein the sensing head comprises at least one sensor, and the immersion probe further comprises at least one sensor contact line connected to at least one connector contact line located on an exterior surface of the connector of the connecting portion of the adjustable portion of the immersion probe.

12. The immersion assembly of claim 11, wherein the second coupling end has an internal cavity and further comprises at least one holder contact line located on an interior surface of the internal cavity, wherein the at least one holder contact line and the at least one connector contact line are in contact and form an electrical connection between the immersion sublance and the immersion probe.

13. An immersion probe configured to connect to an immersion sublance to form an immersion assembly for a converter furnace, the immersion probe comprising: a casing comprising an upper portion and having an internal cavity; and an adjustable portion located in the internal cavity, the adjustable portion comprising a connecting portion, an elastic portion, and a fixed portion, wherein the connecting portion is attached to the elastic portion and the elastic portion is attached to the fixed portion; wherein the adjustable portion extends longitudinally along the internal cavity of the casing from the connecting portion to the fixed portion; wherein the connecting portion comprises a connector attached to a connection base, wherein the connector is located within the internal cavity of the casing, and wherein the connection base is attached to the elastic portion; wherein the elastic portion is disposed between the fixed portion and the connecting portion so that compression of the elastic portion decreases a length of the adjustable portion after a first contact point is established between a surface of the connection base of the connecting portion and a coupling surface of an immersion sublance; wherein the elastic portion is configured to compress until a second contact point is established between the upper portion of the casing and a guide surface of an immersion sublance; wherein the internal cavity of the casing is configured to accept a second coupling end of an immersion sublance; and wherein the connector is configured to be accepted into an internal cavity of the second coupling end of an immersion sublance.

14. The immersion probe of claim 13, wherein the elastic portion comprises a spring, an elastic ring, an elastomer, or any other elastic material.

15. The immersion probe of claim 14, wherein the elastic portion comprises a spring.

16. The immersion probe of claim 13, wherein the immersion probe is substantially cylindrical in shape.

17. The immersion probe of claim 13, further comprising a sensing head.

18. The immersion probe of claim 17, wherein the sensing head comprises a temperature sensor, or an oxygen sensor, or a sampling chamber, or a combination of any thereof.

19. The immersion probe of claim 17, wherein the sensing head comprises at least one sensor, and the immersion probe further comprises at least one sensor contact line connected to at least one connector contact line located on an exterior surface of the connector of the connecting portion of the adjustable portion of the immersion probe.

* * * * *